(12) United States Patent
Aufrichtig et al.

(10) Patent No.: US 6,256,372 B1
(45) Date of Patent: Jul. 3, 2001

(54) APPARATUS AND METHODS FOR STEREO RADIOGRAPHY

(75) Inventors: Richard Aufrichtig, Mountain View, CA (US); Jeffrey Alan Kautzer, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/268,788

(22) Filed: Mar. 16, 1999

(51) Int. Cl.[7] .................................................... A61B 6/02
(52) U.S. Cl. ................................................ 378/41; 378/42
(58) Field of Search ........................................ 378/41, 42

(56) References Cited

U.S. PATENT DOCUMENTS

| | | | | |
|---|---|---|---|---|
| 3,382,362 | * | 5/1968 | Tokuyama et al. | 378/41 |
| 3,984,684 | * | 10/1976 | Winnek | 378/41 |
| 4,095,110 | * | 6/1978 | Bunch | 378/26 |
| 4,214,267 | * | 7/1980 | Roese et al. | 378/42 |
| 4,737,972 | * | 4/1988 | Schoolman | 378/41 |
| 5,661,309 | * | 8/1997 | Jeromin et al. | 250/580 |
| 5,818,064 | * | 10/1998 | Kohgami et al. | 250/580 |

\* cited by examiner

*Primary Examiner*—David P. Porta
*Assistant Examiner*—Allen C Ho
(74) *Attorney, Agent, or Firm*—Craig A. Fieschko, Esq.; DeWitt Ross & Stevens S.C.; Christian G. Cabou, Esq.

(57) ABSTRACT

A digital radiographic imaging system is described which includes an automatic X-ray exposure sequence during which two consecutive images of a target are obtained from two views separated by a translation of the X-ray emitter, wherein such translation is oriented generally parallel to the plane of the X-ray detector. The two images acquired by the digital X-ray detector may then be combined using stereo reconstruction to generate a three-dimensional image of the interior of the target. The three-dimensional combination of images allows for better radiographic definition of clinical objects of interest, thereby increasing a radiologist's ability to detect and distinguish between normal and pathological structures.

17 Claims, 1 Drawing Sheet

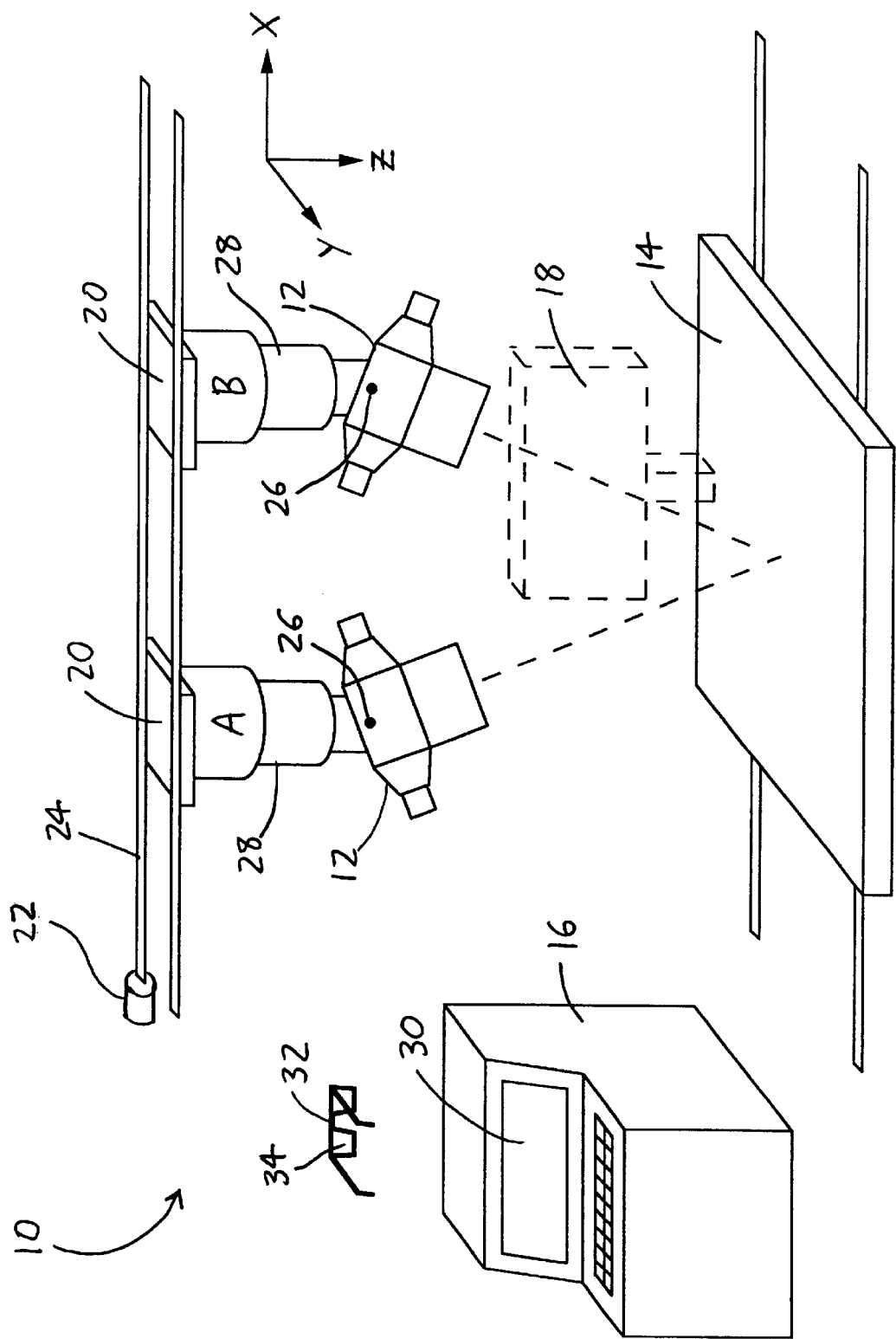
THE FIGURE

APPARATUS AND METHODS FOR STEREO RADIOGRAPHY

FIELD OF THE INVENTION

This disclosure concerns an invention relating generally to radiographic imaging, and more specifically to apparata and methods for generating stereoscopic (three-dimensional) radiographic images.

BACKGROUND OF THE INVENTION

The classic radiographic or "X-ray" image is obtained by situating an object to be imaged between an X-ray emitter (i.e., an X-ray tube) and an X-ray detector. Emitted X-rays pass through the object to strike the detector, with the response of the detector varying over its area as a function of the intensity of the incident X-rays. Since the intensity of the X-rays incident on the detector is largely a function of the density of the object along the path of the X-rays, the detector receives a shadow image of the object which may then be viewed and analyzed by X-ray technicians, e.g., radiologists. In the case of analog radiographic systems, the detector is formed of X-ray film, whereas digital radiographic systems have solid-state detector components (e.g., scintillator/photodiode arrays) whereby the image is provided in electronic form.

One difficulty which is commonly encountered with the analysis of radiographic images is the proper identification of objects contained within the image. As an example, the identification of organs and other body structures is particularly important in radiographic thoracic imaging (the taking of chest X-rays). In the most common type of chest X-ray, a patient will place his/her chest against a detector and the emitter will be activated to send X-rays through the patient from the posterior-to-anterior direction and into the detector. When the image is captured, a radiologist must then systematically evaluate the image to identify the chest wall, diaphragm, lungs, pleura, mediastinum, etc. To properly identify and analyze matters of medical importance, it is desirable to be able to identify extremely small objects on the image, e.g., details as small as 0.7–2.0 mm near the center of the lungs and 0.3–2.0 mm near their periphery. However, it is difficult for a radiologist to identify objects this small on a two-dimensional image, particularly since some objects may be overlapping and their boundaries may be difficult to accurately discern.

SUMMARY OF THE INVENTION

The invention, which is defined by the claims set out at the end of this disclosure, is directed to apparata and methods of stereo radiographic imaging which allow a three-dimensional view of the interior of an X-rayed target, thereby making it easier to see and accurately identify small objects therein. The invention is preferably implemented using a standard digital radiographic imaging system, wherein an X-ray emitter may be activated to emit an X-ray beam through a target and towards a digital X-ray detector. An image of a target resting between the X-ray emitter and the X-ray detector is thereby generated on the X-ray detector. When the invention is in use, the X-ray emitter is initially activated to emit the X-ray beam from a first imaging position relative to the X-ray detector to thereby obtain a first image of the target. The X-ray emitter is then moved by an actuator along a path in an imaging plane oriented at least substantially parallel to the X-ray detector until the X-ray emitter is situated in a second imaging position relative to the X-ray detector. The X-ray emitter is then activated to emit the X-ray beam from the second imaging position to thereby obtain a second image of the target. Because of the different locations of the X-ray emitter when obtaining the first and second images, the first and second images will display parallax, that is, an apparent displacement of objects contained within the images due to the displacement of the X-ray emitter. The first and second images can then be stereoscopically combined so as to be perceived by a viewer as a single three-dimensional image, for example, by alternately displaying the first and second images in rapid succession and masking each of a viewer's right and left eyes in synchronization with the display so that each eye sees only one of the images. If the displays of the first and second images are alternated rapidly enough (e.g., several times per second), the separate images will be perceived as a single image owing to the persistence of vision and the parallax within the images will be perceived as depth.

In this method, it is also possible to provide the X-ray detector with an actuator so that it may be moved instead of (or in addition to) the X-ray emitter, to thereby locate the X-ray emitter in the different first and second imaging positions relative to the X-ray detector. It is notable that if both of the X-ray emitter and the X-ray detector are moved—for example, in opposite directions along parallel paths—each need only be moved by half of the distance that the X-ray emitter or X-ray detector alone would need to be moved in order to generate the same parallax. This can be advantageous insofar as smaller and less expensive actuators can be used to effect the motion. Additionally, since the emitter and detector are simultaneously moved by lesser distances, lesser time is necessary to obtain the overall motion. This can be helpful insofar as it is often desirable to obtain both of the first and second images within the time that a patient can comfortably hold his/her breath.

It is also desirable to orient the X-ray emitter differently when it is resting in the first and second imaging positions so that the axes of the X-ray beams emitted at the first and second imaging positions intersect, preferably at or close to the X-ray detector. In other words, when the X-ray emitter and/or X-ray detector are translated to situate the X-ray emitter in the first and second imaging positions relative to the X-ray detector, it is also preferable to rotate the X-ray emitter and/or X-ray detector so that the axes of the emitted X-ray beams are always centered on the same area on the X-ray detector. This will have the effect of centering the first and second images about approximately the same area on the detector (and target). Since both images will then feature substantially the same imaged objects, this allows a greater effective field of view when the first and second images are stereoscopically combined.

Advantageously, the invention also allows for the measurement of the depths of objects located within the first and second images. Since the relative locations of the X-ray emitter and X-ray detector are known when the X-ray emitter is at the first and second imaging positions, and since the source-to-image distance (SID) between the X-ray emitter and X-ray detector is generally known, this data can be related to the distances between objects contained within the first and second images to allow calculation of the depths of these objects within the target.

It is noted that the invention can also obtain and stereoscopically combine more than two images of the target. As an example, three images of the target may be successively obtained, each from a different imaging position. All of the images, or selected pairs of the images, may then be stereoscopically combined. It should be apparent that a stereoscopic combination of any one pair of images will provide a different view of the target than a different pair of the images. Further, some known methods of stereoscopic combination allow combination of numerous images to provide a three-dimensional image, for example, where the several images are interleaved and then viewed through a lens array which generates a three-dimensional view from the images.

Further advantages, features, and objects of the invention will be apparent from the following detailed description of the invention in conjunction with the associated drawing.

BRIEF DESCRIPTION OF THE DRAWINGS

The FIGURE is a perspective view of an exemplary embodiment of a stereo radiography system in accordance with the present invention.

DETAILED DESCRIPTION OF PREFERRED EMBODIMENTS OF THE INVENTION

The accompanying FIGURE of the drawings illustrates a first exemplary embodiment of a stereo radiography system, which is generally designated by the reference numeral 10. The primary components of the illustrated system 10 includes an X-ray emitter 12 and an X-ray detector 14 between which a target to be X-rayed may be situated, and a processing and display station 16 wherein controls for the emitter 12 and detector 14 are provided and at which images of the X-rayed target are displayed. It is noted that the emitter 12 is shown twice in the FIGURE not because two emitters 12 are required by the inventor, but rather to depict the motion of the emitter 12 from a first imaging position A to a second imaging position B. Each of the foregoing components will now be discussed in turn.

The X-ray emitter 12 is mounted on a trolley 20 which may be actuated (e.g., by actuator 22) to ride on tracks 24 to allow the trolley 20 to translate along a path oriented generally parallel to the plane of the X-ray detector 14, i.e., in the x direction illustrated in the FIGURE. For reasons that will be discussed in greater detail below, the X-ray emitter 12 is also preferably mounted to the trolley 20 by a pivot 26 which allows the X-ray emitter 12 to be actuated to rotate about an axis parallel to the X-ray detector 14, and perpendicular to the path of translation of the X-ray emitter 12. Thus, where the horizontally oriented X-ray detector 14 is used (i.e., the X-ray detector 14 is in the xy plane), the pivot 26 allows actuation of the X-ray emitter 12 to rotate about the illustrated y axis. Apart from moving in these two degrees of freedom, the X-ray emitter 12 and trolley 20 could be adapted to translate and/or rotate in other dimensions as well. For example, a telescoping column 28 may be provided between the trolley 20 and the X-ray emitter 12 to allow the X-ray emitter 12 to translate in the z direction; the column 28 can be situated on tracks/slides on the trolley 20 to translate in the y direction; additional pivots could be provided to allow rotation of the X-ray emitter 12 about the x and z axes; etc. While these motions enhance the versatility of the invention, they are not required. For purposes of the invention, the X-ray emitter 12 need only be able to translate in at least one dimension oriented generally parallel to the plane of the X-ray detector 14, and it is also particularly preferable that the X-ray emitter 12 be able to rotate about at least one axis parallel to the plane of the X-ray detector 14.

Regarding the actuator 22, any number of known servomotor systems or other actuators may be used to drive the trolley 20 along the tracks 24 and about the pivot 26. In practice, the actuator 22 and tracks 24 may be provided by equipping standard General Electric Medical Systems S3805XT Radiographic Suspension System tracks with VIOLIN and SDC servomotor/controller systems (Elmo Motion Control Ltd., Petach-Tikuva, Israel).

The X-ray detector 14, which has a substantially planar configuration as noted above, is a digital detector rather than an analog detector. It is noted that while the detector 14 is illustrated as being horizontally oriented, as is common where detectors are provided in combination with observation tables, the detector 14 could be provided in a variety of other orientations (as exemplified by the vertically-oriented detector 18 shown in phantom lines in the FIGURE). As will be discussed at greater length below, similarly to the X-ray emitter 12, the X-ray detector 14 may also be adapted to allow it to translate and/or rotate relative to the X-ray emitter 12. As an example, within the FIGURE, the tracks 26 allow the X-ray detector 14 to linearly translate with respect to the X-ray emitter 12. Motion of the X-ray detector 14, if provided, may be in lieu of or in addition to motion of the X-ray emitter 12. If both the X-ray emitter 12 and the X-ray detector 14 are adapted for motion, their translation should preferably occur along parallel paths, and their rotation should preferably occur about parallel axes.

In the foregoing arrangement, a target to be radiographically imaged is situated between the X-ray emitter 12 and the X-ray detector 14 (or 18) so that emitted X-rays pass through the target to strike the X-ray detector, as in standard radiographic imaging systems. A controller (which is not shown but which is preferably included within the processing and display station 16) then translates the X-ray emitter 12 along the tracks 24 by a sufficient distance that images generated by the X-ray emitter 12 and X-ray detector 14 before and after translation will display parallax separation between objects within the images. The translation and imaging steps ideally take place during a time period which is sufficiently short that a patient can comfortably hold his/her breath (preferably no more than six seconds, and more preferably on the order of one second or less). As will be discussed below, the images can then be combined to create a stereoscopic (three-dimensional) view of the target. In general, a stereoscopic image of high resolution may be generated when the angle swept by the X-ray emitter 12 with respect to the midpoint of its sweep on the X-ray detector 14 measures between 3–8 degrees. For a standard SID (source-to-image distance, i.e., the distance between the X-ray emitter 12 and X-ray detector 14) of 180 centimeters, an 8 degree angle corresponds to a translation of approximately 25 centimeters for the X-ray emitter, whereas a 3 degree angle corresponds to a translation of approximately 9.5 cm. Such distances are readily achievable by servomotors of reasonable quality within the timeframe of a patient breath hold.

Once the initial and final images are obtained, they are processed by some form of means for generating a stereoscopic view of the target area from the initial and final images. In the imaging system 10 illustrated in FIG. 1, the processing and display station 16 includes a display screen 30 whereupon the initial and final images are displayed in rapid alternating succession. A pair of eyeglasses 32 are then provided wherein a pair of ports 34 is defined, one for each of a viewer's eyes. The ports 34 are each adapted to rapidly open and close in alternating succession in synchronization with the alternating images on the display screen 30; thus, one of the initial and final images is always viewed through one port 34, and the other of the initial and final images is always viewed through the other port 34. Stereoscopic view generators of this type are known and are provided (for example) by the CrystalEyes system (StereoGraphics Corporation, San Rafael, Calif., USA), wherein the ports 34 of the eyeglasses 32 are liquid crystal displays which allow a viewer's left eye to see only one of the initial and final images and the right eye to see only the other image, with the display screen 30 alternating the initial and final images 120 times per second. As a result, a human viewer effectively perceives the separate images as a single three-dimensional image. Advantageously, the CrystalEyes eyeglasses 32 communicate with the display screen 30 by an infrared signal, and thereby a number of eyeglasses 32 may be worn by a number of viewers simultaneously with complete freedom of movement within 8–10 feet of the processing and display station 16. Other means for stereoscopically combining the separate images can additionally or alternatively be used in place of the CrystalEyes scheme, with almost any such means known to the prior art being suitable for use in the invention. As examples, dual images can be combined using a wide variety of known means whereby each port of a pair of eyeglasses 32 masks one image from view (e.g., as in common red/green "3-D glasses"), and greater numbers of images can be combined by interleaving the images and providing lens arrays or screens which only allow certain portions of certain images to be visible from certain angles.

Because the processing and display station 16 receives and processes images in digital form, locations of objects contained within the images can be compared and their depths within the target may be quantified, If the visual separation angle between the target/detector 14 is known (and it generally will be since the source-to-image distance is generally known or easily measurable, and the distance between the initial and final locations of the X-ray emitter 12 are known), the depths of objects within the target may be readily calculated using standard stereo calculations. This step can be performed, for example, by providing a movable cursor on the display screen 30 whereby viewers can select particular objects, and the processing and display station 16 can then perform the measurements and calculations necessary to display the calculated depths of the selected objects.

As noted above, it is preferable to couple the translation of the X-ray emitter 12 with rotation of the emitter 12 in a plane which is parallel to the path along which the X-ray emitter translates, and also perpendicular to the plane of the X-ray detector 14. Such rotation is desirable so that the X-ray beam may be centered about the same area on the X-ray detector 14 in both the initial and final positions A and B of the X-ray emitter 12 (as illustrated in FIG. 1). This rotation is not absolutely necessary since a suitable stereographic image may be constructed from images taken when the X-ray emitter 12 is simply translated within a plane parallel to the X-ray detector 14. However, the combination of such images will suffer from a reduction in the width of field since each image will contain portions of the target that the other does not, and these areas of the images cannot be stereographically combined.

As also noted above, in lieu of translating the X-ray emitter 12, it is instead possible to translate the X-ray detector 14 and obtain images of the target prior to and after such translation. In this situation, only the detector 14 need be moved and the X-ray emitter 12 can be maintained immobile (or can be rotated so that both of the initial and final images are centered about the same area on the target/detector 14). Since this arrangement merely reverses the relative motion of the X-ray emitter 12 and X-ray detector 14, this allows essentially the same images as when only the emitter 12 is moved.

In further embodiments of the invention, both of the X-ray emitter 12 and the X-ray detector 14 may be moved simultaneously in opposite directions to effect the positioning of the emitter 12 with respect to the detector 14. This arrangement can allow the extent of translation and/or rotation of each of the X-ray emitter 12 and/or X-ray detector 14 to be reduced by as much as one-half, thereby requiring lesser time for the emitter 12 and detector 14 to achieve positioning in their initial and final locations. While this is seemingly not very significant, it is nevertheless quite advantageous insofar as the X-ray emitter 12 and/or X-ray detector 14 may be somewhat massive, and lesser ranges in motion can allow the use of lower-priced servo/control systems, lesser delay times between obtaining the initial and final images (and thus lesser time in which a patient must hold his/her breath), and/or gentler acceleration schemes during translation (resulting in lesser oscillation in the X-ray emitter 12 and X-ray detector 14 upon stopping, which is helpful since such oscillation can lead to loss of resolution in the stereoscopic image).

While the X-ray emitter 12 is illustrated as being mounted to the ceiling and the X-ray detector 14 as being mounted to a floor, it should be understood that the X-ray emitter 12 and/or X-ray detector 14 can be mounted in many other arrangements as well. As examples, the X-ray emitter 12 could be mounted to translate along the floor and/or wall, the X-ray detector 14 could translate along a wall and/or ceiling, etc.

The invention is not intended to be limited to the preferred embodiments described above, but rather is intended to be limited only by the claims set out below. Thus, the invention encompasses all alternate embodiments that fall literally or equivalently within the scope of these claims. It is understood that in the claims, means plus function clauses are intended to encompass the structures described above as performing their recited function, and also both structural equivalents and equivalent structures. As an example, though a nail and a screw may not be structural equivalents insofar as a nail employs a cylindrical surface to secure parts together whereas a screw employs a helical surface, in the context of fastening parts, a nail and a screw are equivalent structures.

What is claimed is:

1. A method of radiographic imaging comprising:
    a. situating a target between an X-ray emitter and a digital X-ray detector, wherein the X-ray detector is at least substantially planar and the X-ray emitter may be activated to emit an X-ray beam toward the X-ray detector, the X-ray beam being centered about an X-ray beam axis;
    b. activating the X-ray emitter to emit the X-ray beam from a first imaging position relative to the X-ray detector, the first imaging position being situated in an imaging plane which is at least substantially parallel to the X-ray detector, thereby obtaining a first image of the target;
    c. rapidly moving the X-ray emitter and/or X-ray detector to situate the X-ray emitter in a second imaging position relative to the X-ray detector, the second imaging position being situated in the imaging plane;
    d. activating the X-ray emitter to emit the X-ray beam from the second imaging position to thereby obtain a second image of the target; and
    e. stereoscopically combining the first and second images, wherein:
        (1) the X-ray beam axis is oriented at different angles with respect to the X-ray detector in the first and second imaging positions, (2) the X-ray beam axis when the X-ray emitter is at the first imaging position intersects the X-ray beam axis when the X-ray emitter is at the second imaging position, and (3) the intersection of the X-ray beam axes is situated at least as distantly away from the X-ray emitter as the X-ray detector.

2. The method of claim 1 wherein the X-ray detector is held immobile and the X-ray emitter is moved.

3. The method of claim 1 wherein the X-ray emitter is held immobile and the X-ray detector is moved.

4. The method of claim 1 wherein both the X-ray emitter and the X-ray detector are moved.

5. The method of claim 4 wherein the X-ray emitter and the X-ray detector are translated along parallel and opposite paths.

6. The method of claim 1 wherein the step of stereoscopically combining the first and second images includes the steps of:

a. alternately displaying the first and second images in rapid succession, and b. simultaneously alternately obscuring the view of the first and second images from each of a viewer's right and left eyes.

7. The method of claim 1 wherein:

a. the X-ray beam axis is oriented at different angles with respect to the X-ray detector in the first and second imaging positions, and b. the X-ray beam axis when the X-ray emitter is at the first imaging position and the X-ray beam axis when the X-ray emitter is at the second imaging position coincide with the same area on the X-ray detector.

8. The method of claim 1 wherein:

a. the X-ray beam axis is oriented at different angles with respect to the X-ray detector in the first and second imaging positions, and b. the X-ray beam axis at the first imaging position is oriented at an angle with respect to the X-ray beam axis at the second position, this angle being greater than 0 degrees and less than 10 degrees.

9. The method of claim 1 further comprising the steps of:

a. measuring the location of the X-ray emitter at the first imaging position;

b. measuring the location of the X-ray emitter at the second imaging position;

c. measuring distances between objects contained in the first image;

d. measuring distances between objects contained in the second image;

e. utilizing the measured locations and distances of steps a.–d. to determine the relative depths of objects in the first and second images.

10. A radiographic imaging system comprising:

a. an X-ray emitter which is actuatable to emit an X-ray beam centered about an X-ray beam axis, b. a digital X-ray detector having a generally planar configuration, the X-ray detector being situated within the path of the X-ray beam to thereby generate an image when the X-ray detector receives the X-ray beam, c. a target area situated between the X-ray detector and the X-ray emitter, wherein a target to be radiographically imaged may be located, wherein at least one of the X-ray emitter and X-ray detector are automatically movable to generate in rapid succession:

a first image of the target area, wherein the X-ray emitter is situated at a first imaging position in an imaging plane which is at least substantially parallel to the plane of the X-ray detector, and a second image of the target area, wherein the X-ray emitter is situated in a second imaging position in the imaging plane;

and wherein:

(1) the X-ray beam axis is oriented at different angles with respect to the X-ray detector in the first and second imaging positions, (2) the X-ray beam axis when the X-ray emitter is at the first imaging position intersects the X-ray beam axis when the X-ray second imaging position, and (3) the intersection of the X-ray beam axes is situated at least as distantly away from the X-ray emitter as the X-ray detector.

11. The radiographic imaging system of claim 10 further comprising an emitter actuator operatively associated with the X-ray emitter, the emitter actuator being actuatable to move the X-ray emitter across a path within the imaging plane.

12. The radiographic imaging system of claim 10 further comprising a detector actuator operatively associated with the X-ray detector, the detector actuator being actuatable to move the X-ray detector across a path parallel to the imaging plane.

13. The radiographic imaging system of claim 12 further comprising an emitter actuator operatively associated with the X-ray emitter, the emitter actuator being actuatable to move the X-ray emitter across a path within the imaging plane.

14. The radiographic imaging system of claim 10 wherein:

the X-ray beam axis is at a first angle with respect to the plane of the X-ray detector when the X-ray emitter is at the first imaging position, and the X-ray beam axis is at a second angle with respect to the plane of the X-ray detector when the X-ray emitter is at the second imaging position.

15. The radiographic imaging system of claim 10 further comprising means for generating a stereoscopic view of the target area from the first and second images.

16. The radiographic imaging system of claim 15 wherein the means for generating a stereoscopic view of the target area includes:

a. a screen whereupon the first and second images are displayed, and b. eyeglasses having two viewing ports wherein each port obscures a respective one of the first and second images from a viewer's eyes.

17. A radiographic imaging system comprising:

a. an X-ray emitter which is actuatable to emit an X-ray beam centered about an X-ray beam axis;

b. a digital X-ray detector having a generally planar configuration, the X-ray detector being situated within the path of the X-ray beam to thereby generate an image when the X-ray detector receives the X-ray beam;

wherein at least one of the X-ray emitter and the X-ray detector are movable in a plane oriented at least substantially parallel to the plane of the X-ray detector, whereby the X-ray emitter may be activated to generate images from different imaging positions relative to the X-ray detector, and wherein:
 (1) the X-ray beam axis is oriented at different angles with respect to the X-ray detector in the different imaging positions,
 (2) the X-ray beam axis when the X-ray emitter is at one of the imaging positions intersects the X-ray beam axis when the X-ray emitter is at any other of the imaging positions, and
 (3) the intersection of the X-ray beam axes is situated at least as distantly away from the X-ray emitter as the X-ray detector;

c. a display providing the images from different imaging positions in rapid alternating succession, and d. eyeglasses having two viewing ports wherein each port alternately obscures the images from different imaging positions in synchronization with the display.

* * * * *